United States Patent [19]

Carter et al.

[11] Patent Number: 4,483,849

[45] Date of Patent: Nov. 20, 1984

[54] STABILIZATION AND PURIFICATION OF INTERFERON WITH PROPYLENE GLYCOL, RESULTING IN A NON-TOXIC PRODUCT

[76] Inventors: William A. Carter; Gerald Silver, both of HEM Research, 5451 Randolph Rd., Rockville, Md. 20852

[21] Appl. No.: 430,755

[22] Filed: Jan. 7, 1983

[51] Int. Cl.³ .................. A61K 45/02; C07G 7/00
[52] U.S. Cl. .................. 424/85; 260/112 R
[58] Field of Search .......... 424/85; 260/112 R; 435/68, 172

[56] References Cited

PUBLICATIONS

Sedmak, J. et al., Methods in Enzymology, vol. 78, pp. 591–593, Academic Press, 1981.
Merck Index, p. 1017, 9th edition, 1976.

*Primary Examiner*—Blondel Hazel
*Attorney, Agent, or Firm*—Cushman, Darby & Cushman

[57] ABSTRACT

A new process for stabilizing purified human interferon is described, using propylene glycol. Propylene glycol also aids in the interferon purification procedure. Older methods used stabilizing agents which are toxic, antigenic or irritating. The new process will make available significantly more interferon of clinical purity for use in patients with cancer, viral illnesses and other diseases as yet undesignated (e.g. multiple sclerosis, amyotropic lateral sclerosis, scleroderma, etc.).

6 Claims, 2 Drawing Figures

STABILIZATION AND PURIFICATION OF INTERFERON WITH PROPYLENE GLYCOL, RESULTING IN A NON-TOXIC PRODUCT

BACKGROUND

The purification and stabilization of human interferon has become increasingly important as its use as an antiviral and anticancer agent grows. The most powerful technique for purifying interferon from media of interferon-producing cells involves binding of the protein to a hydrophobic ligand carrying primary amino groups, such as Cibarcron Blue F3G-A, and its subsequent elution by solutions containing ethylene glycol (Jankowski, et al., 1976, Biochemistry 15:5182–5187; Knight and Fahey, 1981, J. Biol. Chem. 256:3609–3611). A slight modification of the procedure starting from "serum-free" media was patented by Knight U.S. patent application No. 84,632, filed Oct. 12, 1979) but in our hands the advantage in purity is more than offset by yields which are diminished 4–10 fold and, more importantly, by the need to use ethylene glycol.

DISADVANTAGES OF ETHYLENE GLYCOL

Ethylene glycol is toxic to human beings. The lethal dose in humans is about 1.4 ml/kg or 100 ml (Merck Index, pp. 3736, 9th Edition). Lower doses can cause central nervous system depression, vomiting, drowsiness, respiratory failure, coma, convulsions, renal damage which may proceed to anuria, uremia and death. Consequently, the presence of ethylene glycol in preparations of interferon severely limits the clinical use of such interferon preparations, particularly for chronic, long-term, drug administration.

We observed that ethylene glycol is much less desirable than propylene glycol in eluting interferon from affinity ligands like various commercial and/or generic products such as Cibacron Blue F3GA, Blue Sepharose CL-6B, AFfi-Gel Blue, Remazol, TM etc. In side-by-side experimentation, we determined that higher yields and smaller volumes are consistently obtained from propylene glycol (Table 1, from Carter and Silver, unpublished results)

TABLE 1
COMPARISON OF ETHYLENE GLYCOL AND PROPYLENE GLYCOL IN ELUTING INTERFERON FROM AFFI-GEL BLUE

| No. of runs | eluant | percent of input recovered | minimum volume of eluant |
| --- | --- | --- | --- |
| 44 | ethylene glycol | 49 | 2495 |
| 23 | propylene glycol | 71 | 260 |

These features have importance because larger volumes require more extensive concentration steps, increasing the probability of encountering serious contamination problems and severe losses in bioactivity and potency. Lower yields reduce the economy of the purification procedure and increase purification difficulties which inevitably result from needing larger amounts of starting material, handling larger volumes, etc. Interferon is probably the most costly human medicinal thus far discovered and, accordingly any steps which increase its cost-effective manufacture are to be greatly coveted and esteemed in value.

Moderate concentrations of ethylene glycol stabilize interferon to some extent. However, the effect is small and high concentrations of ethylene glycol may actually destabilize interferon (Table 2: from Heine et al., 1978, Arch. Virol. 57:185–188 and Carter and Horoszewicz, 1980, Pharm. Ther. 8:359–377).

TABLE 2
STABILITY OF HUMAN INTERFERON β TO ETHYLENE GLYCOL

| Storage temperature | % of ethylene glycol | Days to loss 70% of activity |
| --- | --- | --- |
| +22 C. | 0 | 5 |
| " | 25 | 30 |
| " | 50 | 30 |
| " | 75 | <1 |
| −70° C. | 0 | 14 |
| " | 30 | 42 |
| " | 40 | 42 |
| " | 50 | 56 |

ADVANTAGES OF PROPYLENE GLYCOL

Propylene glycol is not toxic. According to the Merck Index (page 7649, 9th Edition) "Taken internally propylene glycol is harmless, probably because its oxidation yields pyruvic and acetic acids." When half of the carbohydrate diet of rats was replaced with propylene glycol for 8 months there was no evidence of toxicity and only slight impairment in growth (Hanzlik et al., 1939., J. Pharmacol. 74:266–251).

Propylene glycol is more desirable than ethylene glycol in eluting interferon from Affi-Gel Blue (Table 1, from Carter and Silver, unpublished results). Propylene glycol can elute more of the interferon activity in a smaller volume, resulting in a significantly more concentrated product. Repeated tests in our laboratory have confirmed this finding and leave no doubt that elution by propylene glycol from purification matrices such as Affi-Gel Blue, Cibacron Blue F3GA, etc. can provide interferon which is some 40 times more concentrated than the product eluted by ethylene glycol.

Our experiments (Carter and Silver, unpublished results) also show that aqueous solutions of 50% propylene glycol have the unique property of stabilizing interferon some 10-fold more than the same solutions lacking propylene glycol.

Thus, the use of propylene glycol is clearly superior to ethylene glycol for interferon purification and storage in that higher yields of a concentrated, stable, non-toxic product can be obtained as described above, as shown in the above cited reference material and as exemplified later in this patent application.

MULTIPLE SPECIES OF INTERFERON

We performed the above cited experiments on natural human interferon β. Similar experiments show that the same results hold true for natural human interferons α and, for natural animal interferons α, β and γ, for natural plant interferon and for cloned species of human interferons. Propylene glycol will show utility for synthetic or "hybrid" interferons of the type described by Streuli et al., (1981. Proc. Natl. Acad. Sci. USA 78:2848–2852) and for other synthetic interferons involving recombinations among, additions to or deletions or modifications of existing natural or synthetic interferons, said other synthetic interferons produced biologically or chemically or by a combination of biological and chemical techniques.

BRIEF DESCRIPTION OF THE PRIOR ART

Jankowski et al., 1976, Biochemistry 15:5182–5187; Knight and Fahey, 1981, J. Biol. Chem. 256:3609–3611; Knight, 1979, U.S. patent application No. 84,632; Merck Index. 9th Edition, pages 3736 and 7649; Heine et al., 1978., Arch. Virol. 57:185–188; Carter and Horoszcewicz, 1980, Pharm. Ther, 8:359–377; Carter and Silver, unpublished results cited in this application.

SUMMARY OF THE INVENTION

Methods and compositions are provided for the stabilization and purification of interferon, resulting in a non-toxic product suitable for clinical use. Interferon containing fluids are attached to a suitable purification matrix, like Remazol TM then interferon is specifically eluted in a small volume with an aqueous solution containing propylene glycol. The product has several properties which are unexpected and which are not characteristic of interferons purified by methods with similar simplicity and economy; namely, the interferon produced with propylene glycol is highly concentrated and very stable. Furthermore, it is in a form suitable for human use as a broad-spectrum medicinal and consequently will be a significant benefit to mankind.

DESCRIPTION OF THE SPECIFIC EMBODIMENTS

Fluids containing natural human interferon $\beta$ can be prepared by superinducing human fibroblasts with double-stranded RNA as described (Carter and Horoszewicz, 1980, Pharm. Ther. 8:359–377) or in serum-depleted media (Knight., 1979, U.S. patent application No. 84,632). Fluids containing natural human interferon $\alpha$ can be prepared by incubating fresh human leukocytes with Sendai virus as described by Strander and Cantell (1966., Ann. Med. Exp. Fenn., 44:265–273.) Fluids containing natural human interferon can be prepared by incubating blood cells with phytohemagglutinin as described by Wheelock (1965, Science, 149:310–311). Fluids containing synthetic human interferon prepared by recombinant DNA techniques can be prepared by growing recombinant microorganisms or recombinant cells in such medium as may be appropriate for interferon production. An almost infinite number of variations are possible in the methods used to generate interferon-containing fluids. All these methods yield fluids from which interferon can be purified according to the process of our invention and accordingly, we consider purification of interferon from all interferon-containing fluids to be included in our invention.

Interferon-containing fluids can be made 1M in NaCl and maintained at neutral pH with sodium phosphate. This material can be applied to a 300 ml bed volume column of Remazol per 10,000 ml of fluid whereupon interferon and some other proteins become absorbed to the column matrix. The column can be washed with 500 ml of 1M NaCl buffered at neutral pH with sodium phosphate, removing many proteins from the column but not removing interferon. The column can then be washed with a 1:1 mixture of 2M NaCl buffered at neutral pH with sodium phosphate and propylene glycol, said mixture referred to as 50% propylene glycol. When fractions of 200 ml are collected, the majority of the interferon activity will ordinarily be recovered in fraction 2.

EXPERIMENTAL

In order to demonstrate the subject invention, the following experiments were carried out with natural human interferon $\beta$.

All temperatures not otherwise indicated are Centigrade.

All percents not otherwise indicated are percents by volume.

EXAMPLE 1

Comparison of propylene glycol and ethylene glycol in eluting interferon from Affi-Gel Blue.

Figure 1:
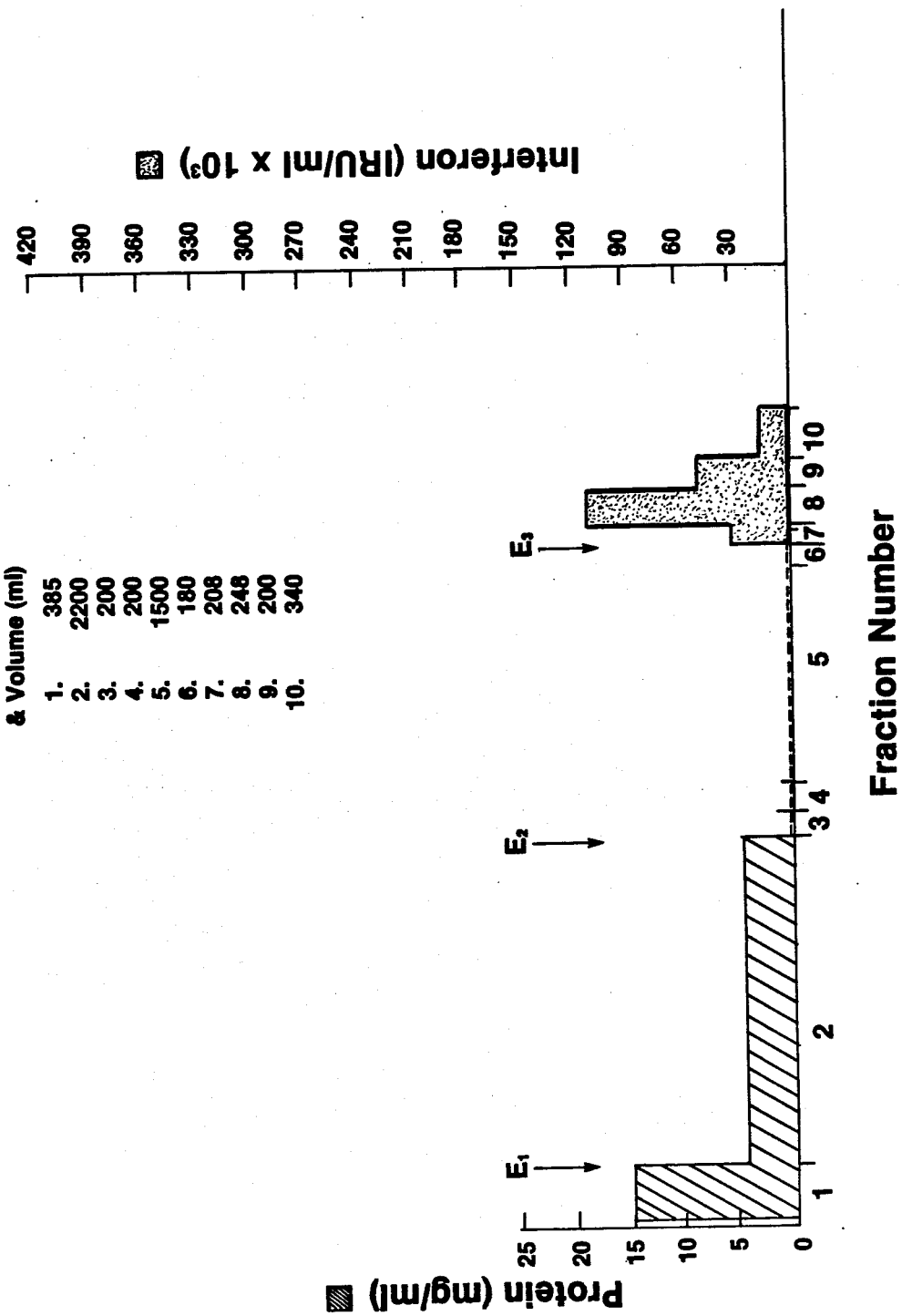
Figure 2:
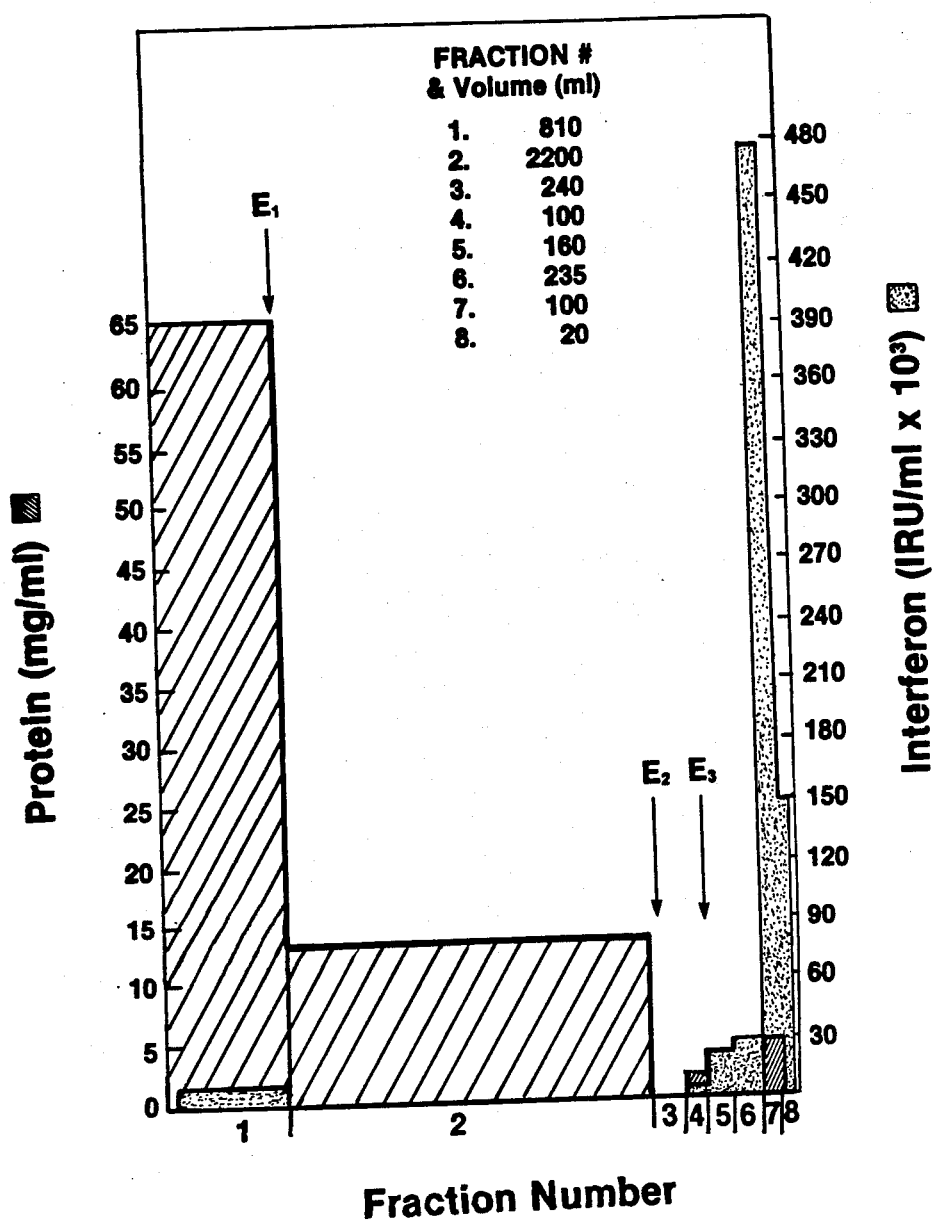

The results of the comparison are shown in FIGS. 1 and 2. In FIG. 1, 385 ml of interferon-containing fluid (52 million units) was applied to a 5 ×20 cm column Affi-Gel Blue (Bio-Rad) previously equilibrated with 1.0M NaCl/PO$_4$. Following absorption, the column was washed with 3 volumes of 1.0M NaCl/PO$_4$ buffer (E$_1$). The column was then "conditioned" with a wash of 50% ethylene glycol in IM NaCl/PO$_4$ buffer (E$_2$) then IF was eluted with 60% PG (E$_3$) collecting fractions at a rate of about 30 ml/cm 2/hr. Fractions were assayed for protein and interferon activity. Fractions 8 and 9 contained the activity peak, resulting in 38 million units of interferon in 448 ml of 60% ethylene glycol.

In FIG. 2, 810 ml of interferon-containing fluid (73 million units) was applied to a 5 ×20 cm column of Affi-Gel Blue previously equilibrated with 1.0M NaCl/PO$_4$ buffer (B$_1$). The column was then washed with 40% propylene glycol in 1.0M NaCl/PO$_4$ buffer (E$_3$), finally IF eluted with 50% PG (E$_3$) collecting fractions at a rate of about 30 ml/cm$^2$/hr. Fractions were assayed for protein and interferon activity. Fraction 7 contained the activity peak, resulting in 47 million units of interferon in 100 ml of 50% propylene glycol.

EXAMPLE 2

The use of propylene glycol in eluting interferon from Remazol (Table 3).

Approximately 2000 ml of interferon $\beta$-containing fluid was made 1M in NaCl buffer at neutral pH with sodium phosphate and containing 10% propylene glycol (Start sample) and adsorbed on a 300 ml bed volume column of Remazol. The material which flowed through unadsorbed to the column was called the SPENT SAMPLE and contained little or no interferon activity. The column was washed with 500 ml of 1M NaCl buffered at neutrality with sodium phosphate (WASH SAMPLE), then interferon was eluted with three fractions of a 1:1 mixture of propylene glycol and IM NaCl buffered at neutral pH wth sodium phosphate (50% PG I, II and III).

TABLE 3

| | ELUTION OF INTERFERON $\beta$ FROM REMAZOL WITH PROPYLENE GLYCOL | | | |
|---|---|---|---|---|
| mg/ml protein | Sample | Volume (ml) | IF titer/ml | Total units |
| .44 | START | 1999 | 49,000 | 97,951,000 |
| .36 | SPENT | 1999 | <1,000 | — |
| .28 | WASH | 500 | <1,000 | — |
| .010 | 50% PG-1 | 210 | <10,000 | — |
| 0.47 | II | 200 | 513,000 | 102,600,000 |
| 0.19 | III | 92 | 27,000 | 2,474,000 |

It can be seen that little or no interferon was lost in the SPENT, WASH or 50% PGI fractions. All (95%)

of the interferon was recovered in Fraction PGII in only 200 ml.

It can be seen from the foregoing that propylene glycol is uniquely potent solvent for the purification and stabilization of interferon. While we have presented specific situations in which propylene glycol was used, we recognize that the field is rapidly changing and we expect that there will occur improvements in column matrices, ionic compositions, propylene glycol concentrations, molecular species of interferon, etc. There may even occur totally new systems for interferon purification. To the extent that these future modifications are compatible with propylene glycol as a superior solvent during purification they are included in our patent. Even in purification processes which may be incompatible with the use of propylene glycol, we anticipate that propylene glycol will be particularly and uniquely useful as a stabilizing storage medium for purified interferon, especially for interferon to be used clinically.

Therefore, we claim:

1. A process for purifying and stabilizing interferon, comprising the steps of:
   adding an interferon-containing fluid to a solid purification matrix;
   eluting said interferon from said matrix with a solution containing propylene glycol; and
   storing said interferon in a solution containing propylene glycol.

2. A process according to claim 1 wherein said solid matrix is a hydrophobic ligand.

3. A process according to claim 1 wherein said solid matrix is Remazol.

4. A process according to claim 1 wherein said solid matrix is Cibacron blue F3G-A.

5. A process according to claim 1 wherein said solid matrix is Affi-gel Blue.

6. A process according to claim 1 wherein said propylene glycol containing solution is a 1:1 mixture of propylene glycol and 1M NaCl buffered at neutral pH with sodium phosphate.

* * * * *